US006675808B2

(12) United States Patent
Karasic

(10) Patent No.: US 6,675,808 B2
(45) Date of Patent: Jan. 13, 2004

(54) INTUBATION PROTECTION DEVICE

(75) Inventor: Brian Lee Karasic, P.O. Box 300547, Houston, TX (US) 77230-0547

(73) Assignee: Brian Lee Karasic, Houston, TX (US)

( * ) Notice: Subject to any disclaimer, the term of this patent is extended or adjusted under 35 U.S.C. 154(b) by 232 days.

(21) Appl. No.: 09/952,967

(22) Filed: Sep. 12, 2001

(65) Prior Publication Data

US 2002/0134391 A1 Sep. 26, 2002

Related U.S. Application Data

(63) Continuation-in-part of application No. 09/625,528, filed on Mar. 26, 2001.

(51) Int. Cl.$^7$ .................................. A61C 5/14
(52) U.S. Cl. .................. 128/859; 128/861; 128/200.26
(58) Field of Search ................. 128/846, 848, 128/859–861, 200.26, 207.14, 207.15, 207.17, DIG. 26, 207.18; 602/902

(56) References Cited

U.S. PATENT DOCUMENTS

| 2,669,988 A | 2/1954 | Carpenter | 128/136 |
| 4,270,531 A | 6/1981 | Blachly | 128/207.14 |
| 4,425,911 A | 1/1984 | Luomanen | 128/200.26 |
| 5,590,643 A | 1/1997 | Flam | 128/200.26 |
| 5,623,924 A | 4/1997 | Linderman | 128/207.17 |

Primary Examiner—Michael A. Brown

(74) Attorney, Agent, or Firm—Wendy Buskop; Buskop Law Group, P.C.

(57) ABSTRACT

A system for use in patient comprising, a first mouthguard and a second mouthguard, each mouthguard having a front, a back, an internal channel and an external surface, wherein each internal channel has an occlusal surface for engaging the patient's teeth, and where the first mouthguard has disposed on the external surface opposite the occlusal surface a first base, and the second mouthguard has disposed on the external surface opposite the occlusal surface, a second base, with the first base connected to a first and second tube and the second base is connected to a third and fourth tube; and wherein the first and second tubes are positioned opposite each other on the first base; and the third and fourth tubes are positioned opposite each other on the second base, and all tubes are located the same distance from the front of the mouthguard; a right wedge with an right upper wedge surface and a right lower wedge surface, wherein the right wedge further comprises (i) an upper right connector extending from the right upper wedge surface supporting an upper right post, and (ii) a lower right connector extending from the right lower wedge surface supporting a lower right post; a left wedge with an left upper wedge surface and a left lower wedge surface, wherein the left wedge further comprises (i) an upper left connector extending from the left upper wedge surface supporting an upper left post, and (ii) a lower left connector extending from the left lower wedge surface supporting a lower left post; wherein the upper right post is inserted into the first tube, the lower right post is inserted into the fourth tube, and the upper left post is inserted into the second tube and the lower left post is inserted into the third tube.

30 Claims, 8 Drawing Sheets

INTUBATION PROTECTION DEVICE

FIELD OF THE INVENTION

The present application is a continuation-in-part application of patent application Ser. No. 09/625,528 filed Mar. 26, 2001.

This invention generally relates to a device, which can be inserted in the mouth of a patient to gain access to the mouth and throat of the patient.

BACKGROUND OF THE INVENTION

Presently there is no device which protects the upper and lower dentition, helps to direct the endotracheal tube into the trachea and helps to visualize the pharyngeal area. There has been a commonly fabricated mouthguard device which is used for several purposes, (1) protection for upper and lower teeth especially while sleeping to prevent damage from grinding and clinching, (2) protect upper and lower teeth while playing any sports where an object or another person might cause damage to the persons teeth, and (3) relaxation of the musculature of the face from bruxing, and thereby protect against myofacial pain dysfunction and even reduce possible damage to temperomandibular joint (TMJ). However, these uses for conventional mouthguards do not make they useful to open the mouth sufficiently to provide a 12.5 to 15 mm opening for a child's throat, and a 17.0 to 21.0 mm opening for an adult throat, which permits the endotracheal tube to easily extend into the trachea. Furthermore, for many years, there has been a need for an intubation protection device that helps to protect the upper and lower dentition from damage during the use of laryngoscope and other similar devices, and a device which helps the physician to visualize the back of the throat for improved operational function.

Devices known in the prior art are in U.S. Pat. Nos. 4,270,531, 4,425,911, 5,623,924, 5,590,643, and 2,669,988. None of these devices provide the flexibility of the present device with a detachable tongue retractor feature, a detachable throat opener, as well as separately engagable and sizable wedges to connect to the respective mouthguards for enabling many different sizes of mouths and types of operations to be accommodated.

SUMMARY OF THE INVENTION

The invention relates to a system for use in patient comprising (a) a first mouthguard and a second mouthguard, each mouthguard having a front, a back, an internal channel and an external surface, wherein each internal channel has an occlusal surface for engaging the patient's teeth, further said first mouthguard has disposed on the external surface opposite the occlusal surface a first base, and said second mouthguard has disposed on the external surface opposite the occlusal surface, a second base, wherein said first base is connected to a first and second tube and the second base is connected to a third and fourth tube; and wherein said first and second tubes are positioned opposite each other on the first base; and said third and fourth tubes are positioned opposite each other on the second base, and all tubes are located the same distance from the front of the mouthguard; (b) a right wedge with an right upper wedge surface and a right lower wedge surface, wherein said right wedge further comprises: (i) an upper right connector extending from the right upper wedge surface supporting an upper right post, and (ii) a lower right connector extending from the right lower wedge surface supporting a lower right post; (c) a left wedge with an left upper wedge surface and a left lower wedge surface, wherein said left wedge further comprises (i) an upper left connector extending from the left upper wedge surface supporting an upper left post, and (ii) a lower left connector extending from the left lower wedge surface supporting a lower left post; wherein said upper right post is inserted into said first tube, said lower right post is inserted into said fourth tube, and said upper left post is inserted into said second tube and said lower left post is inserted into said third tube.

DETAILED DESCRIPTION OF THE PREFERRED EMBODIMENTS

The invention relates to a device that extends acrylic from the maxillary teeth down to the mandibular portion of the device. Instead of having a convex (upper) and concave lower shape, both devices can be flat and smooth.

Figure 1:
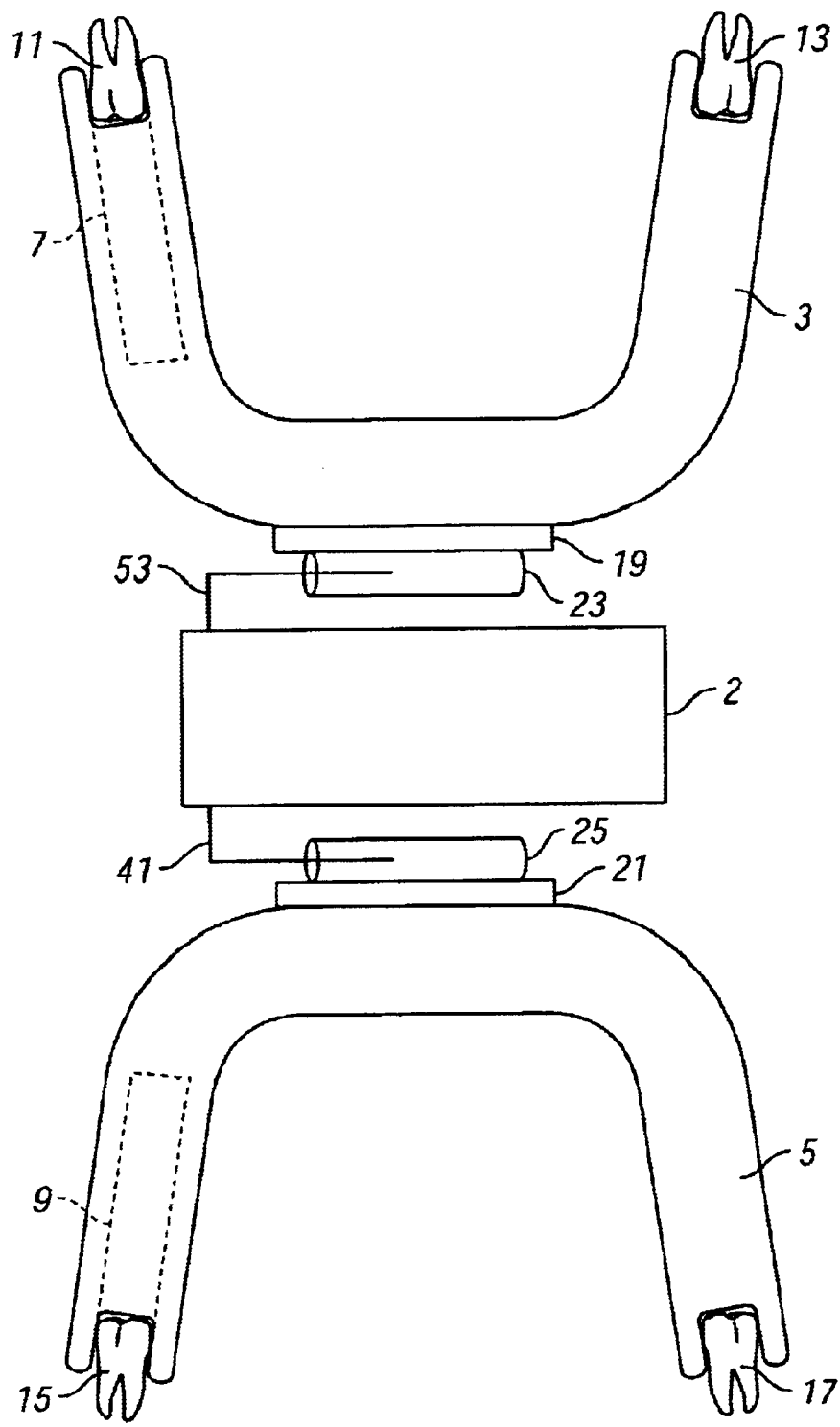
FIG. 1 is a side view of the system of the invention inserted in a patient's mouth.

FIG. 1 shows the invention is a system for use in a patient having a first mouthguard 3 and a second mouthguard 5 each mouthguard having a front, a back, an internal channel and an external surface. Specifically, mouthguard 3 has internal channel 7 and mouthguard 5 has internal channel 9. Each internal channel has an occlusal surface for engaging the patient's teeth. In FIG. 1, the upper teeth are 11 and 13, and the lower teeth are shown as 15 and 17. The first mouthguard 3 has disposed on the external surface opposite the occlusal surface a first base 19. The second mouthguard 5 has disposed on its external surface opposite the occlusal surface, a second base 21.

Figure 2:
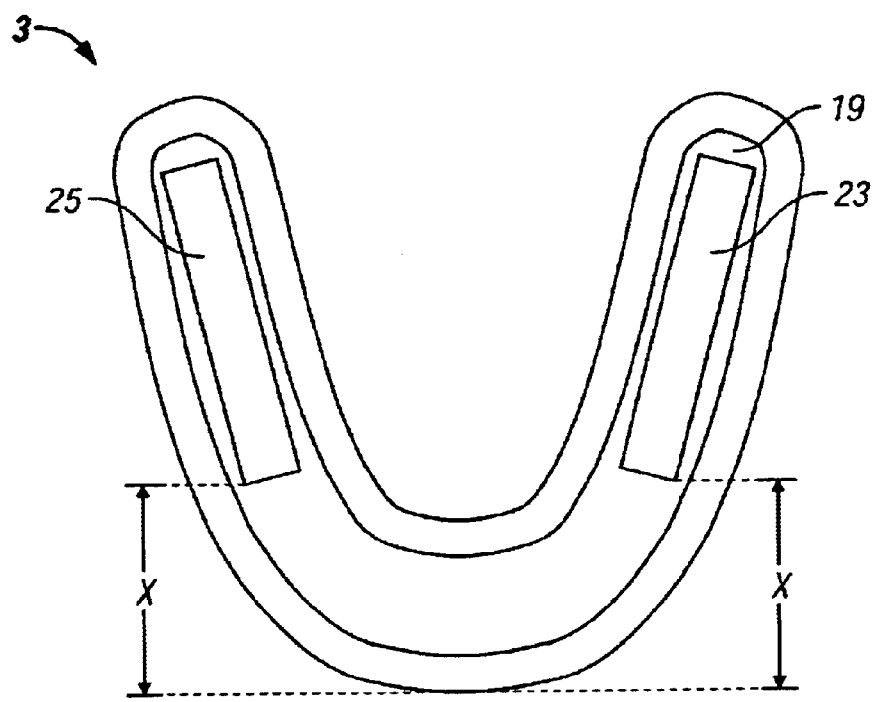
FIG. 2 is a bottom view of an upper mouthguard according to the present invention.
Figure 3:
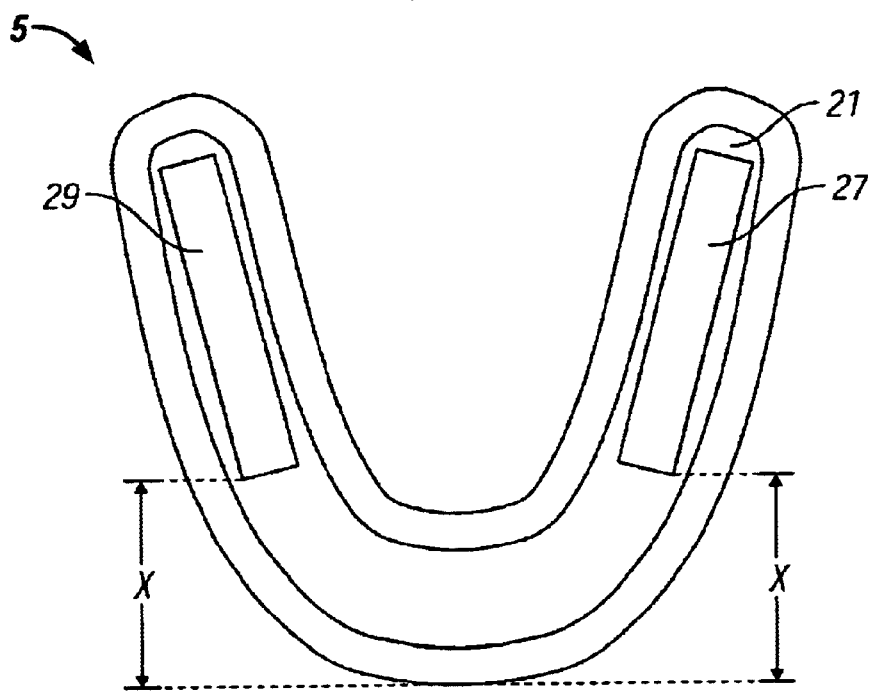
FIG. 3 a top view of the lower mouthguard according to the present invention.

FIG. 2 shows a bottom view of mouthguard 3. The first base 19 is connected to a first tube 23 and a second tube 25. FIG. 3 is a top view of mouthguard 5, wherein the second base 21 is connected to a third tube 27 and fourth tube 29. As can be seen in both FIG. 2 and FIG. 3, the first and second tubes 23 and 25 are positioned opposite each other on the first base 19. The third and fourth tubes 27 and 29 are positioned opposite each other on the second base 21. All four tubes are located the same distance from the front of the mouthguard. For an adult, it is contemplated that a preferred distance from the front of the mouthguard would be between about 23 to 27 mm, preferably about 25 mm, and for a child, the distance is contemplated to range from about 12 to 17 mm and most preferably be about 17 mm.

Figure 4:
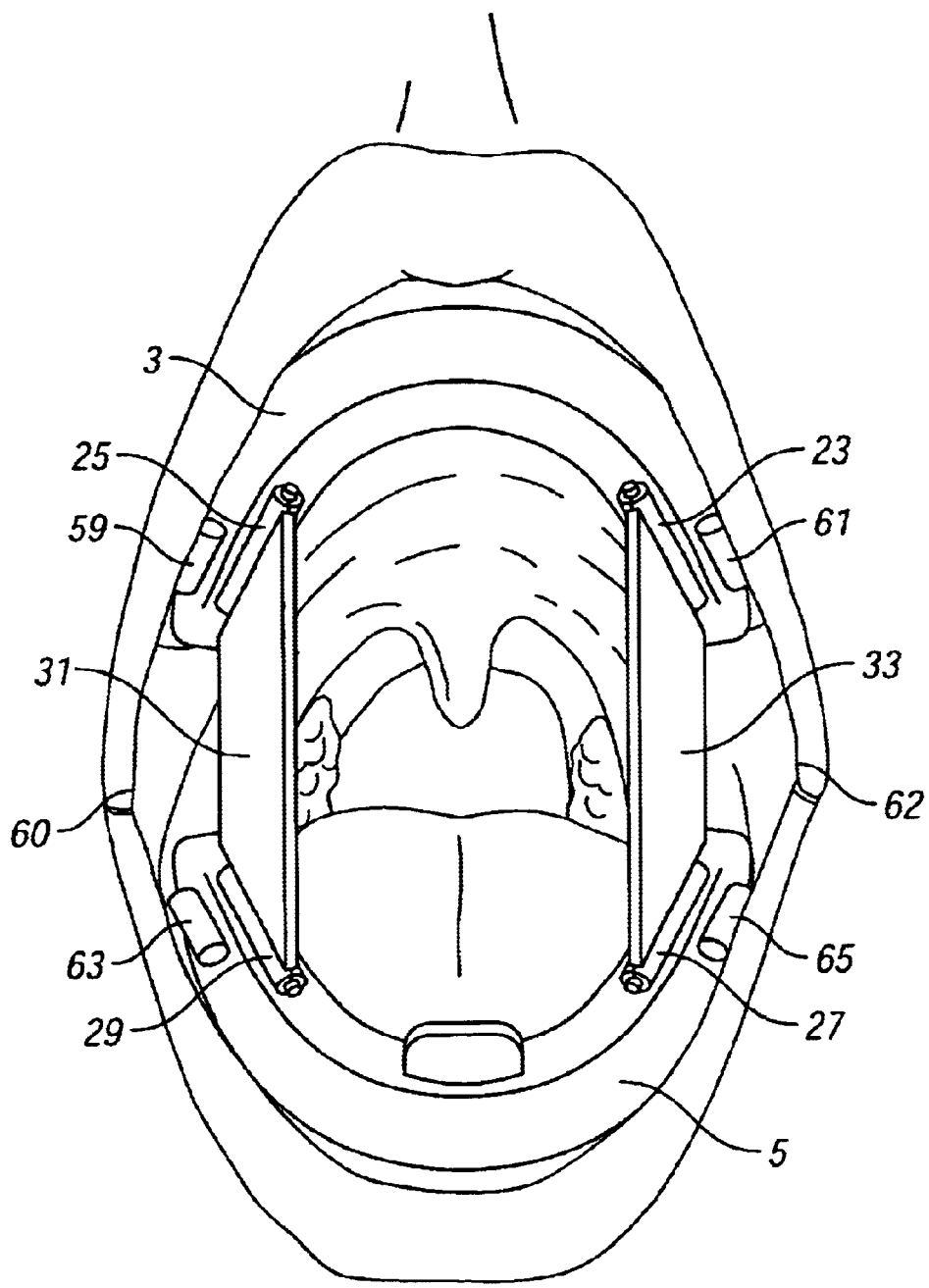
FIG. 4 is a front view of the assembled invention in a patient's mouth.
Figure 5:
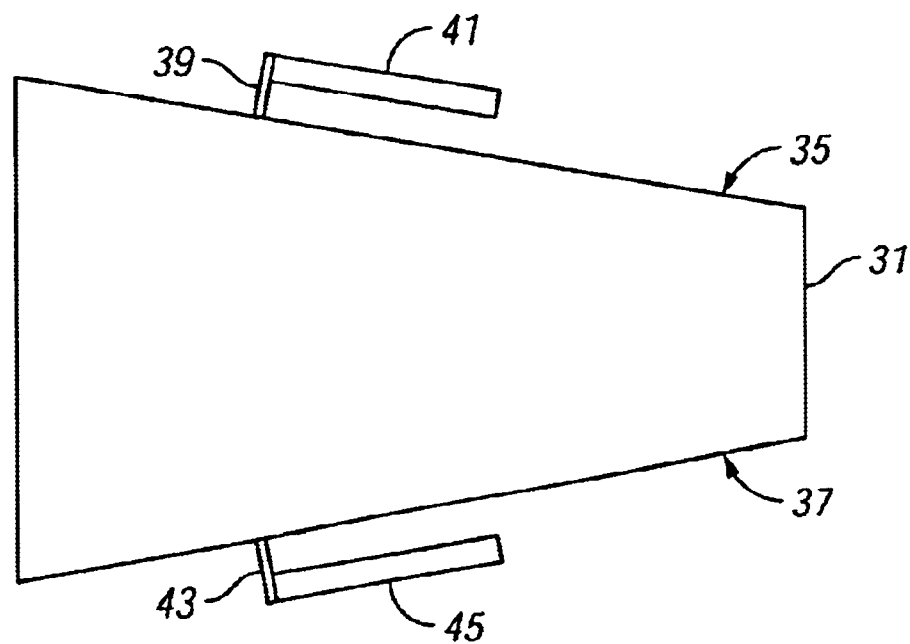
FIG. 5 is the side view of each wedge according to the invention.
Figure 5:
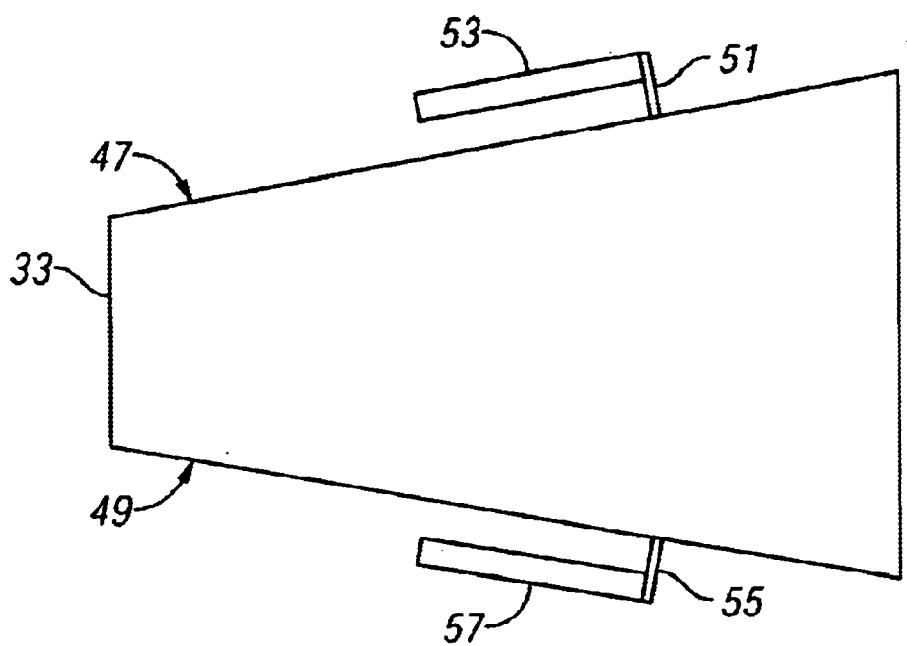

The invention requires that two wedges be used with the two mouthguards to hold open the mouth of the patent. As shown in FIG. 4, which is front view of the invention a right wedge 31 is between tube 25 and tube 29 and a left wedge 33 is disposed between tube 23 and tube 27. Although in the most preferred embodiment, it is contemplated that both wedges 31 and 33 have the same basic construction it is contemplated to be within the scope of the invention that one wedge could be smaller than the other wedge or have a different shape. The most preferred shape for the wedge 31 and or 33 is a rhomboid. Further details on the construction of wedge 33 are shown in FIG. 5. Both wedges 31 and 33 are shown in FIG. 5. Right wedge 31 has a right upper wedge surface 35 and a right lower wedge surface 37. Right wedge 31 has an upper right connector 39 extending from the right upper wedge surface 35 supporting an upper right post 41. A lower right connector 43 extends from the right lower wedge surface 37 supporting a lower right post 45. The left wedge 33 has a left upper wedge surface 47 and a left lower wedge surface 49. An upper left connector 51 extending from the left upper wedge surface 47 supporting an upper left post 53. A lower left connector 55 extends from the left lower wedge surface 49 supporting a lower left post 57.

To use the invention, the upper right pest 41 is inserted into the first tube 25, the lower right post 45 is inserted into said fourth tube 29, and the upper left post 53 is inserted into the second tube 23 and the lower left post 57 is inserted into the third tube 27.

In the most preferred embodiment, the mouthguards 3 and 5 are maxillary and mandibular or upper and lower teeth mouthguards. In the most preferred embodiment, the mouthguards 3 and 5 are intubation mouthguards, which have as integral components, the base and the tube for engaging the wedge.

The most preferred mouthguards would be mouthguards made by the Thermoguard Company, such as model 3147 available from Benshoff Company of Albany, N.Y. Similarly, impact mouthguards can be used in this invention, which are also available from Benshoff Company of Albany. The most usable material in the mouthguards can be either Molloplast-B a brand available from Zahn Dental Lab, alternatively, nickel-chromium materials would work, as well as chromium cobalt, Vitallium 2000 as well as alternative materials from acrylic materials available from Thermoguard.

Flexible mouthguards are very usable and enable the device to be used in the mouths of severly traumatized patients, or very old patients who have extreme stiffness of joints, and difficulty in opening the mouths.

Figure 6:
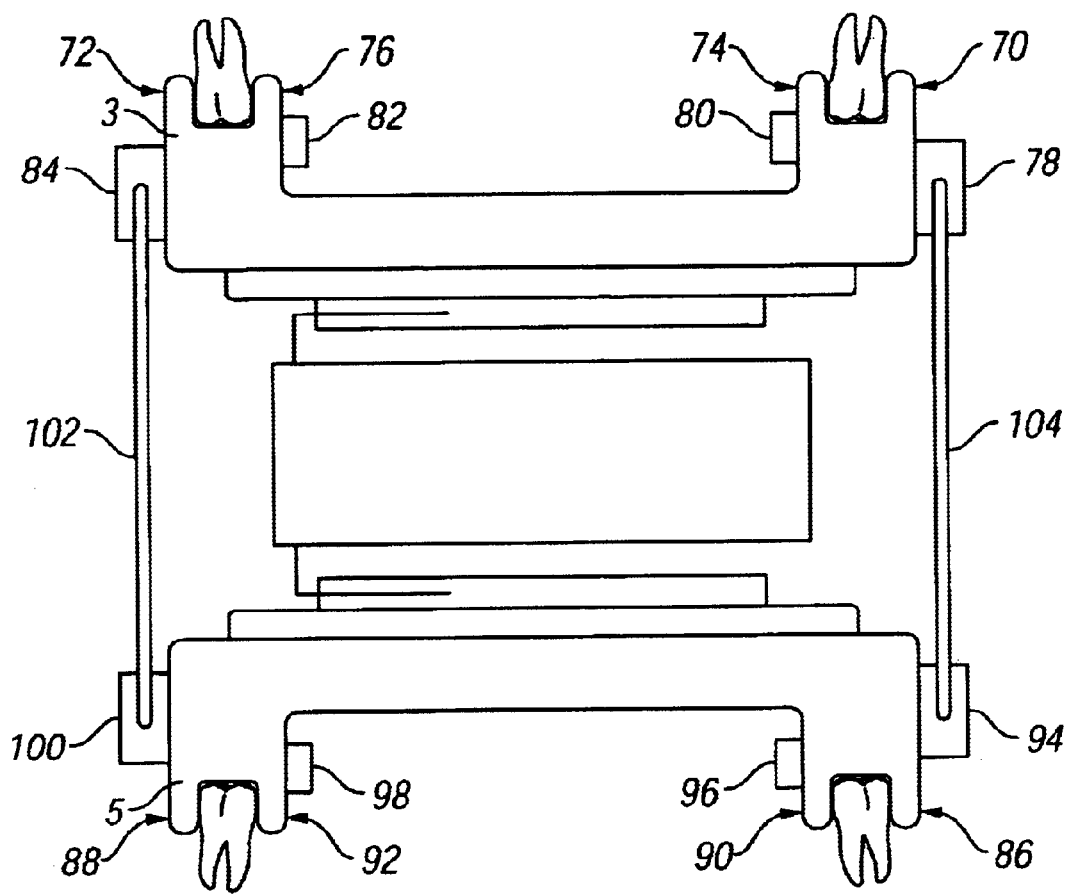
FIG. 6 is a back of the assembled invention in the patient's mouth.

In the most preferred embodiment, the mouthguards each have a plurality of fasteners. As shown in FIG. 6, first mouthguard (3) has a first right check side (70) and a first left check side (72), first right tongue side (74) and first left tongue side (76) and further comprises four fasteners, a first fastener (78), second fastener (84), third fastener (82) and fourth fastener (80), each disposed on the external surface of the first mouthguard, and the second mouthguard (5) has a second right check side (86), a second left cheek side (88), a second right tongue side (90) and a second left tongue side (92) and further a fifth fastener (94) is disposed on second right cheek side (86), sixth fastener (96) is disposed on second right tongue side (90), seventh fastener (98) is disposed on second left tongue side (92) and eighth fastener (100) is disposed on second left cheek side (88), a first throat opener (102) engagable with fourth fastener (84) and eighth fastener (100) and a second throat opener (104) engageble with first fastener (78) and fifth fastener (94). The extra tongue side fasteners can be used to support a light source or a micro camera.

Typical throat openers considered as usable in this invention include any one of either a Finnoshetti Retractor, a Tufftier Retractor, or a buffered pointess, a Crow Davis Mouth Gag, or a Jennings Mouth Gag. It is contemplated that one type of retractor could be used on one side of a patient's mouth and another type could be used on the other side of the patient's mouth, so combinations of these retractors could also be used.

Figure 7:
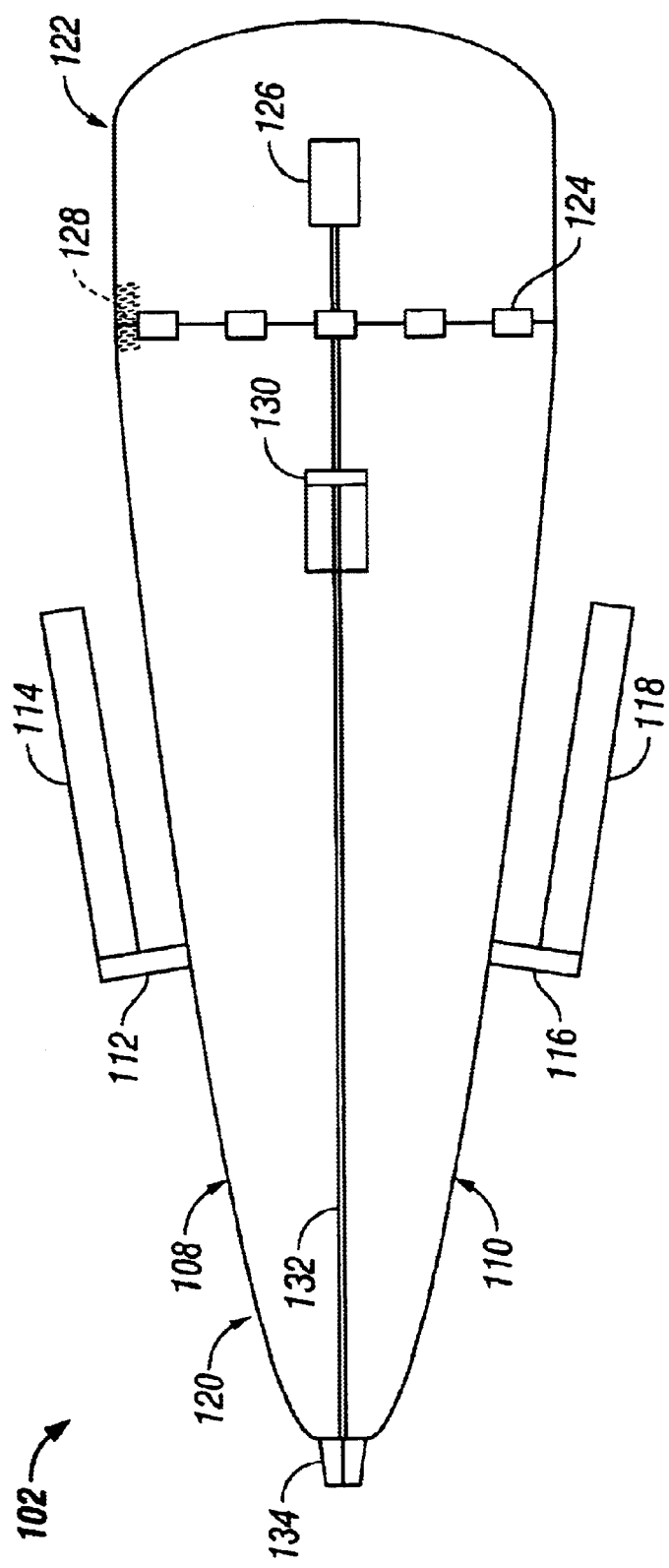
FIG. 7 is a top view of a throat opener usable with the present invention.

FIG. 7 shows the first throat opener (102) comprises: a body (106) having an upper surface (108) and a lower surface (110), an upper connector (112) extending from upper surface (108) engaging upper post (114), a lower connector (116) extending from lower surface (110) engaging a lower post (118).

The body (106) is at least a two-part construction having a first half (120) and second half (122) connected by a hinge (124). The hinge (124) comprises a mechanism (126) for extending and retracting the first half (120) from said second half (122). The mechanism (126) is a spring and ratchet wherein spring (128) engages first half (120) to extend first half (120) away from second half, and ratchet (130) pulls first half (120) towards second half (122) using wire (132) engaging a rotating connection (134).

It should be noted, that except for the spring described above, all components of the invention could be made from hard acrylic, such as Lucitone 199, manufactured by Dentsply of York, Pa.

In an alternative embodiment, wedge 2, can be made from a metal or metal alloy, such as nickel, chromium, chromium cobalt, carbide steel, stainless steel or coated metals. The most usable metals of the invention contemplated to be chrome-cobalt alloys, which are nickel and beryllium free. It can be made from a metal, such as nickel, chromium, carbide steel, and stainless steel.

Figure 8:
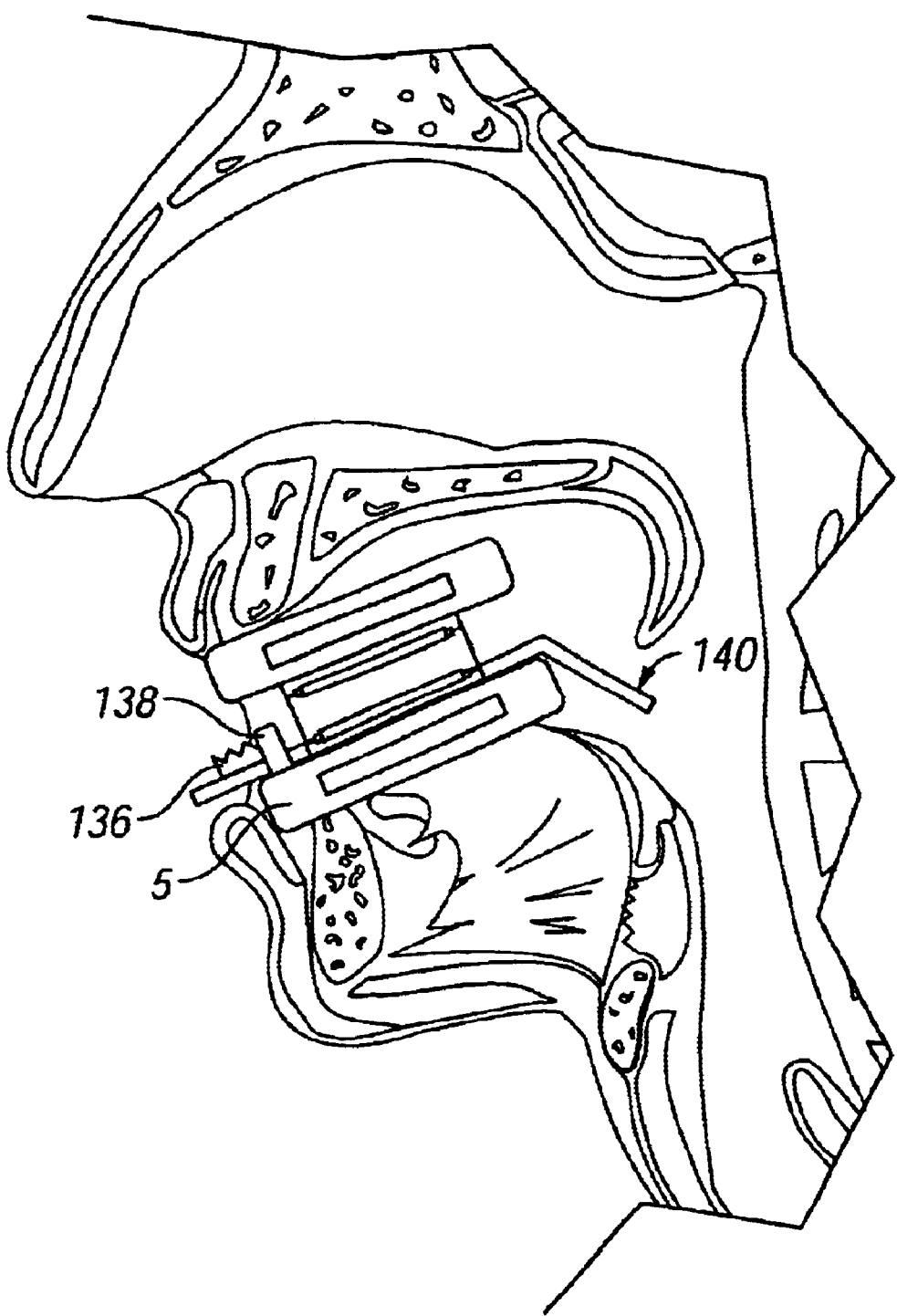
FIG. 8-side view of the system of the invention inserted in a patient's mouth showing the tongue retractor embodiment.

FIG. 8 shows an alternative embodiment of the system further comprising a tongue depressor holder (136) disposed near the front of a mouthguard (5), preferably the lower mouthguard, and wherein the holder is located on an external surface of the mouthguards. The tongue depressor fastener (138) for slidably engaging a tongue depressor (140) FIG. 9 shows the detail of a tongue depressor, wherein tongue. depressor (140) has a flattening portion (142) and back portion (144), and a plurality of ridges (146) disposed on the back portion for engaging with the tongue depressor fastener.

Figure 9:
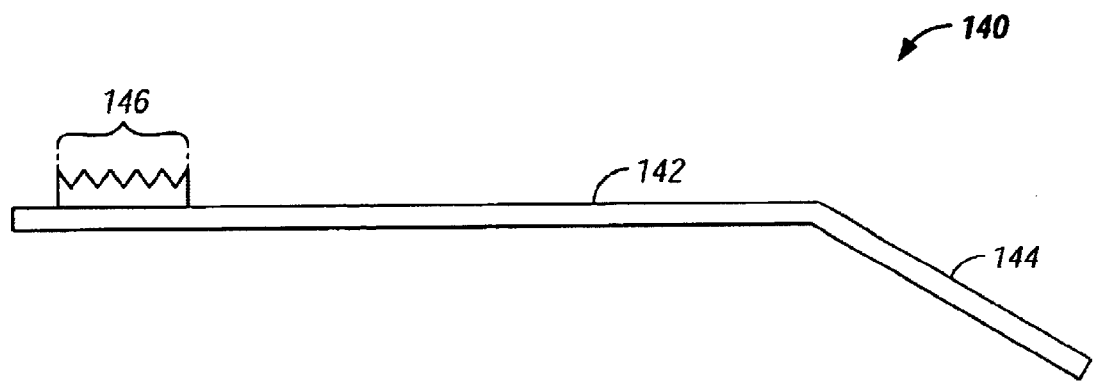
FIG. 9 is side view of the tongue retractor of the present invention.
Figure 10:
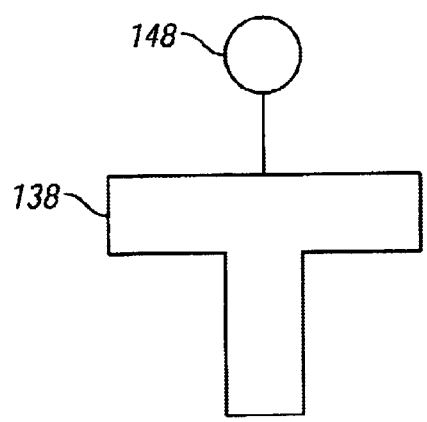
FIG. 10 is a side view of a tongue depressor fastener with handle of the present invention.

FIG. 10 provides a detail of the tongue depressor fastener (138), which comprises a T shaped body for acting as a stop in between the ridges (146) shown in FIG. 9, of tongue depressor (140). The tongue depressor fastener (138) can further comprises a handle (148) for raising and lower the tongue depressor fastener. In a preferred embodiment, the tongue depressor (140) has a shape with rounded edges, which is longer than it is wide. The shape could be any one of the shapes, rectangular, oval, or dog bone.

In still another embodiment, the invention contemplates a fiber optic light source secured to a mouthguard. In the most preferred embodiment, this fiber optic light source is secured to the mouthguard disposed on the lower teeth of said patient. An Olympus brand fiber optic system could be used.

In yet another embodiment of the invention, the system can utilize one or more micro cameras disposed at least one mouthguard for viewing the throat of a patient.

Still other variations of this invention contemplated different constructions for the base disposed on the mouthguard, For example, it is contemplated that a base made in segments could be usable, that is first base can consist of a first segment and a second segment, and the second base comprises a third segment and a fourth segment.

Regarding the materials usable in the invention, it is contemplated that the mouthguards be made from material, which is elastomeric. The mouthguards could be made from an off the shelf molded product, or they could be custom molded to the patient's teeth. In another embodiment, it is contemplated that the mouthguards, base, connectors and tubes are made from rigid material, such as an acrylic polymer or possibly from a self-molding material, or it is possible, that the posts and connectors could be made from metal. If a self-molding material is used for the internal channel of the mouthguard, it is contemplated that the material Aquasil from Caulk/Dentsply could be used. It is also contemplated that the external material for the mouthguard could be a bioplast, such as Thermoguard available from Great Lakes Supply.

It is further contemplated to be within the scope of the invention that the system be made in parts, and then glued together for lower cost in manufacture. In such an embodiment, parts like the connectors could simply be glued to the posts. Similarly, the tubes could be glued to the base. A glue contemplated as usable in this invention to attach the base to the mouthguard, or to glue any of the components would be cyanoacrylicate glue, such as Hotstuff Super T, available from Satellite City Corp.

Alternatively, the construction of the system a removably detachable construction is contemplated, for example, the tubes could be threadably engaged with the bases, and similarly, the connectors could be threadably engaged with the posts.

The system is designed so that it could be used by a dentist or an anesthesiologist, for example to intubate a patient during surgery. Alternatively, a dentist could use it during simple root canals to give greater room in the patient's mouth for complicated work.

The tubes 23 and 25 can be made from hard acrylic, such as Lucitone 199, manufactured by Dentsply of York, Pa. In an alternative embodiment, the tubes can be made from a metal or metal alloy, such as nickel, chromium, chromium cobalt, carbide steel, stainless steel or coated metals. The most usable metals of the invention contemplated to be chrome cobalt alloys, which are nickel and beryllium free.

The bases 21 and 19 can be made from hard acrylic, such as Lucitone 199, manufactured by Dentsply of York, Pa. In an alternative embodiment, the bases can be made from a metal or metal alloy, such as nickel, chromium, chromium cobalt, carbide steel, stainless steel or coated metals. The most usable metals of the invention are contemplated to be chrome cobalt alloys, which are nickel and beryllium free.

While this invention has been described with emphasis on the preferred embodiments, it should be understood that within the scope of the appended claims, the invention might be practiced other than as specifically described herein.

What is claimed is:

1. A system for use in patient comprising,
   (a) a first mouthguard and a second mouthguard, each mouthguard having a front, a back, an internal channel and an external surface, wherein each internal channel has an occlusal surface for engaging the patient's teeth, further said first mouthguard has disposed on the external surface opposite the occlusal surface a first base, and said second mouthguard has disposed on the external surface opposite the occlusal surface, a second base, wherein said first base is connected to a first and second tube and the second base is connected to a third and fourth tube; and wherein said first and second tubes are positioned opposite each other on the first base; and said third and fourth tubes are positioned opposite each other on the second base, and all tubes are located the same distance from the front of the mouthguard;
   (b) a right wedge with a right upper wedge surface and a right lower wedge surface, wherein said right wedge further comprises (i) an upper right connector extending from the right upper wedge surface supporting an upper right post, and (ii) a lower right connector extending from the right lower wedge surface supporting a lower right post; and
   (c) a left wedge with a left upper wedge surface and a left lower wedge surface, wherein said left wedge further comprises (i) an upper left connector extending from the left upper wedge surface supporting an upper left post, and (ii) a lower left connector extending from the left lower wedge surface supporting a lower left post;
   wherein said upper right post is inserted into said first tube, said lower right post is inserted into said fourth tube, and said upper left post is inserted into said second tube and said lower left post is inserted into said third tube.

2. The system of claim 1, wherein first mouthguard has a first right check side and a first left check side and further comprises two fasteners, a first fastener and second fastener, each disposed on the external surface of the first mouthguard, and said second mouthguard has a second right check side, a second left cheek side, and further comprises two fasteners, a right check side fastener and a left cheek side fastener with each fastener disposed on the external surface of the second mouthguard, wherein the first fastener is disposed on first right check side and the second fastener is disposed on first left check side, the right cheek side fastener is disposed on second right cheek side and the left cheek side fastener is disposed on second left cheek side, a first throat opener engages first fastener and second fastener and a second throat opener engages right cheek side fastener and left cheek side fastener.

3. The system of claim 2, wherein said first throat opener comprises: a body having an upper surface and a lower surface, an upper connector extending from upper surface engaging upper post, a lower connector extending from lower surface engaging a lower post.

4. The system of claim 3, wherein said body has a shape, which is, wedged shape.

5. The system of claim 3, wherein said body is at least a two part construction having a first half and second half connected by a hinge.

6. The system of claim 5, wherein said hinge comprises a mechanism for extending and retracting said first half from said second half.

7. The system of claim 6, wherein said mechanism is a spring and ratchet mechanism wherein spring engages first half to extend first half away from second half, and ratchet pulls first half towards second half using a rotating connection.

8. The system of claim 2, wherein said fasteners are disposed on the external surface that faces the cheeks of said patients.

9. The system of claim 2, wherein said throat opener is selected from the group comprising: a Finnoshetti Retractor, a Tufftier Retractor, and a buffered pointess, a Crow Davis Mouth Gag, a Jennings Mouth Gag and combinations thereof.

10. The system of claim 1, further comprising a tongue depressor holder disposed near the front and on a external surface of one of said mouthguards, a tongue depressor fastener for slidably engages a tongue depressor, wherein tongue depressor has a flattening portion and back portion, and a plurality of ridges disposed on the back portion for engaging said tongue depressor fastener.

11. The system of claim 10, wherein said tongue depressor fastener comprises a T shaped body for acting as a stop in between the ridges of said tongue depressor.

12. The system of claim 11, wherein said tongue depressor fastener further comprises a handle for raising and lower said tongue depressor fastener.

13. The system of claim 10, wherein said tongue depressor has a shape with rounded edges that is longer than it is wide.

14. The system of claim 10, wherein said tongue depressor is a shape selected from the group: rectangular, oval, or dog bone.

15. The system of claim 1, further comprising a fiber optic light source secured to a mouthguard.

16. The system of claim 15, wherein said fiber optic light source is secured to the mouthguard disposed on the lower teeth of said patient.

17. The system of claim 1, further comprising at least one micro camera disposed at least one mouthguard for viewing the throat of said patient.

18. The system of claim 1, wherein said first base comprises a first segment and a second segment, and said second base comprises a third segment and a fourth segment.

19. The system of claim 1, wherein said mouthguards are made from material which is elastomeric.

20. The system of claim 1, wherein said mouthguards are made from a member of the group, molloplast-B, nickel chromium, chromium cobalt and Vitallium 2000.

21. The system of claim 1, wherein said mouthguards are made from molded material.

22. The system of claim 1, wherein said mouthguards, base, connectors and tubes are made from rigid material.

23. The system of claim 1, wherein said mouthguards, base, connectors and tubes are made from an acrylic polymer.

24. The system of claim 1, wherein said mouthguards are custom molded to a patient's teeth.

25. The system of claim 1, wherein said mouthguards are made from self-molding material.

26. The system of claim 1, wherein said connectors are glued to said posts.

27. The system of claim 1, wherein said tubes are glued to said base.

28. The system of claim 1, wherein said tubes are threadably engaged with said bases.

29. The system of claim 1, wherein said connectors are threadably engaged with said posts.

30. The system of claim 1, wherein said system is used to intubate a patient.

* * * * *